(12) United States Patent
Lundmark

(10) Patent No.: US 6,174,535 B1
(45) Date of Patent: Jan. 16, 2001

(54) HYDRATED HONEY GEL POLYMERIC COMPOSITIONS AND PROCESS FOR PREPARING SAME

(76) Inventor: Larry D. Lundmark, 4520 Embassy Cir., NE., Prior Lake, MN (US) 55372

( * ) Notice: Under 35 U.S.C. 154(b), the term of this patent shall be extended for 0 days.

(21) Appl. No.: 09/340,634

(22) Filed: Jun. 28, 1999

(51) Int. Cl.$^7$ ........................................ A61K 7/00

(52) U.S. Cl. .................... 424/401; 424/486; 424/487; 424/488; 514/844; 514/847; 514/873; 514/949

(58) Field of Search ..................... 424/401, 486, 424/487, 488; 514/844, 847, 873, 949

(56) References Cited

U.S. PATENT DOCUMENTS

| | | | |
|---|---|---|---|
| 4,423,041 | 12/1983 | Clum et al. | 424/184 |
| 4,863,725 | 9/1989 | Deckner et al. | 424/81 |
| 4,917,890 | 4/1990 | McAnalley | 424/195 |
| 5,501,849 | 3/1996 | Lee | 424/59 |
| 5,626,853 | 5/1997 | Bara et al. | 424/101 |
| 5,688,831 | 11/1997 | El-Nokaly et al. | 514/938 |
| 5,746,945 | 5/1998 | Ryklin et al. | 252/309 |
| 5,798,111 | 8/1998 | Kanga et al. | 424/401 |

*Primary Examiner*—S. Mark Clardy
*Assistant Examiner*—Michael A. Williamson
(74) *Attorney, Agent, or Firm*—Forrest L. Collins

(57) ABSTRACT

This invention deals with the delivery of liquid polysaccharides to a cosmetic and toiletry products. A unique formulation is prepared which permits the incorporation of honey into such cosmetic and toiletry products.

32 Claims, No Drawings

HYDRATED HONEY GEL POLYMERIC COMPOSITIONS AND PROCESS FOR PREPARING SAME

BACKGROUND OF THE INVENTION

1. Field of the Invention

The purpose of this invention is to provide an effective method of incorporating liquid polysaccharides which are normaly sticky into a product while avoiding the problem of stickiness. This invention thus describes hydrated polymeric compositions containing honey which may be utilized to treat keratinous substrates such as skin and hair.

2. Description of the Art Practices

Pure natural honey contains sugar secretions and are collected from honeycombs. Honey also contains natural proteins, minerals, vitamin B1, vitamin B2, vitamin C, and nicotinic acid all of which makes honey desirable for use as a natural ingredient for cosmetics. Honey has been used as a fragrance ingredient and humectant in skin conditioners. Honey has also been employed as a biological additive in shampoos, face, body and hand creams and lotions; bath products, hair conditioners, cleansing products, moisturizing creams and lotions, and in paste masks (mud packs).

Honey is typically used at very low levels in cosmetic products due to an undesirable stickiness associated with the presence of a high level of solubilized polysaccharides. A feeling of tackiness results when pure natural honey is applied to keratinous substrates, such as skin or hair. Thus, the use of honey in significant quantities in cosmetic and toiletries has heretofore been limited.

U.S. Pat. No. 5,626,853 to Bara et al., issued May 6, 1997 relates to a gel containing an aqueous phase, a hydrophilic polymer as a gelling agent, a coloring material which is soluble or dispersible in the aqueous phase and at least one organopolysiloxane solubilized in the aqueous phase. The Bara et al., patent describes the gel as usable in the cosmetics field for making up both the face and the human body.

U.S. Pat. No. 5,688,831 issued Nov. 18, 1997 to El-Nokaly et al., describes a make-up composition in the form of a water-in-oil emulsion comprising a silicone phase, humectant, pigment and organic amphiphilic material capable of forming smectic lyotropic liquid crystals in the product or on the skin.

Clum et al., in U.S. Pat. No. 4,423,041 issued Dec. 27, 1983 describes a detackifying composition for use in emulsion-type personal care compositions comprising a mixture of a silicone fluid and a silicone wax in a ratio of from about 9:1 to 1:3. McAnalley, in U.S. Pat. No. 4,917,890 issued Apr. 17, 1990 discusses a process for producing aloe extracts including the separation of the leaves of the aloe plant into distinct portions.

U.S. Pat. No. 4,863,725 to Deckner issued Sep. 5, 1989 relates to a clear oil-free, non-greasy skin moisturizing composition which includes as the major component a copolymer of glycerol and methacrylic acid polyglyceryl-methacrylate together with a polyol to enhance skin feel, one or more preservatives and water, and optionally one or more thickeners, one or more skin soothing agents, such as allantoin and/or dl-panthenol, one or more astringents, and/or one or more colorants.

Lee, in U.S. Pat. No. 5,501,849 issued Mar. 3, 1996 discloses an emollient composition, having a stated use in a method of treating a psoriasis in which abnormal skin is exposed to actinic or ultraviolet radiation, comprising a lipophilic emollient, wherein the composition is a non-viscous liquid which, on application to skin or a like surface, spreads to provide a substantially uniform coating of the lipophilic emollient, and wherein the coating does not absorb a significant amount of the incident actinic or ultra-violet radiation and is sufficiently non-volatile to persist for a period of sufficient length, for a therapeutically effective dose of incident radiation to be administered.

Ryklin et al., in U.S. Pat. No. 5,746,945 issued May 5, 1998 discusses water-in-oil emulsions which comprising (a) water; (b) from about 10 to 65% by weight of an oil; and (c) an emulsification system comprising a polysiloxane poly-alkyl polyether copolymer and a phthalic anhydride derivative, substantially permanently maintaining the water and oil as an emulsion, the emulsification system and the emulsification system being substantially free from alumi-num and zirconium salts, the emulsion being at a pH of from about 5 to 10.

U.S. Pat. No. 5,798,111 issued to Kanga et al., Aug. 25, 1998 describes clear emulsion cosmetic compositions that include an aqueous phase having 2-methyl-1,3-propanediol and an oily phase containing silicones, especially cyclom-ethicone and a cyclomethicone-dimethicone copolyol sili-cone fluid mixture. The compositions described by Kanga et al., are stated to exhibit visual clarity and can be formulated into a cold cream or antiperspirant/deodorant which are highly phase stable and insensitive to shear decomposition while being processed.

To the extent that the foregoing references are relevant to the present invention, they are herein specifically incorpo-rated by reference. Where temperatures are given, they are in degrees Celsius unless otherwise indicated. Percentages and ratios given herein are by weight unless otherwise indicated. Measurements herein are stated in degrees of approximation and where appropriate the word "about" may be inserted before any measurement. Ranges and ratios maybe combined.

SUMMARY OF THE INVENTION

The present invention describes a composition of matter comprising polyglycerylmethacrylate; and, a liquid polysac-charide component.

The present invention further describes a composition of matter comprising polyglycerylmethacrylate; a liquid polysaccharide component; and, a silicone based compo-nent.

Yet a further aspect of the present invention is a compo-sition of matter comprising polyglycerylmethacrylate; a liquid polysaccharide component; a silicone based component, and, a glycol.

The present invention also describes a substantially homogeneous hydrated honey gel polymeric composition prepared by the process of (A) dispersing honey in polyglycerylmethacrylate, (B) mixing the honey and the polyglycerylmethacrylate for a sufficient period of time to form a hydrated honey gel polymeric composition, and a process for preparing the same.

Further described herein is a process for preparing a substantially homogeneous hydrated honey gel polymeric composition by:

(A) dispersing honey in polyglycerylmethacrylate; and, (B) mixing the honey and the polyglycerylmethacrylate to form a substantially homogeneous mixture, (C) combining with the substantially homogeneous mix-ture a silicone based component, and (D) mixing the resultant mixture for a sufficient period of time to form a substantially homogeneous translucent homogeneous hydrated honey gel polymeric composition.

DETAILED DESCRIPTION OF THE INVENTION

The first component of the present invention to be discussed is the polyglycerylmethacrylate component. The polyglycerylmethacrylate component is a highly crosslinked polymer.

The polyglycerylmethacrylate is in the form of a transparent gel containing from about 50 to about 75% by weight solids, and may or may not contain incidental ingredients, such as propylene glycol which may be present in an amount of 2% or less. A preferred polyglycerylmethacrylate is Lubrajel CG, a registered trademark of United Guardian Inc., which is distributed by International Specialty Products of Wayne N.J. The preferred form of Lubrajel CG has a viscosity at 20 degree C. (Brookfield RTV) ranging from about 400,000 to about 5,000,000, a specific gravity of 1.2 mg/ml, is completely soluble in water and is substantially stable at 250 degree. F., and on sealed storage for 3 years at 20 degree. C. Lubrajel CG is a clathrate formed by the reaction of glycerin and methylmethacrylate.

Lubrajel CG can best be described as a hydrated polymeric complex, the water of hydration of which is subject to change with the humidity of the atmosphere to which it is exposed. Lubrajel CG has been described as a clathrate formed by the reaction of sodium glycerate with a methacrylic acid polymer, stabilized with a small amount of propylene glycol.

Lubrajel CG is characterized by its non-allergenic properties and its excellent moisturizing qualities which have been confirmed by skin impedance measurements. The bound water in Lubrajel CG ranges from as little as one-third to as much as 58%. The free water ranges from 5–20%. The conversion of the clathrate to the hydrate causes a rapid drop in viscosity. When Lubrajel CG is diluted with water, the end result is largely free water, resulting in a drop in viscosity, depending upon the particular grade.

The liquid polysaccharide component is usually a sugar. A sugar being defined as a material having hydroxy, ketose, or aldose moieties and which is sweet to the taste. A preferred source of the liquid polysaccharide component is honey.

Honey consists chiefly of dextrose and levulose (70–80%) polysaccharides with smaller amounts of water, sucrose (2–10%), dextrin, wax, proteins, volatile oil, mineral acids, and coloring and flavoring components, based on derivative plant source. The polysaccharide in the liquid polysaccharide component is typically a mixture of levulose and dextrose.

Other sources of the liquid polysaccharide component includes corn syrup. The corn syrup contains glucose and fructose. In particular, high fructose corn syrup is preferred when corn syrup is employed. Mixtures of high fructose corn syrup and honey may be effectively utilized in the present invention.

Volatile methyl siloxanes (cyclomethicone) and linear polydimethylsiloxanes (dimethicone) have been important ingredients in cosmetic and toiletry products for over 40 years. These two classes of siloxanes represent a very significant portion of the silicones used in personal care products.

Siloxanes are a specific class of silicones which can be divided into volatile methyl siloxanes, because of their vapor pressure and low heat of vaporization, and linear polydimethylsiloxanes. Cyclomethicone and Dimethicone *International Cosmetic Ingredient Dictionary and Handbook* designations for preferred silicone based component, e.g. siloxanes.

These siloxane materials typically have good functional properties (such as spreadability, slip, and substantivity). They also have pleasant aesthetic properties (they are smooth, silky, non-oily, non-greasy, and non-tacky). Being water insoluble, siloxanes are not compatible with honey and therefore cannot be simply combined with honey to eliminate tackiness.

Of particular interest in the compositions of the present invention are where the silicone based component is a dimethicone, dimethiconol, cyclomethicone tetramer, and cyclomethicone pentamer, and mixtures thereof.

A desirable component for use herein is a glycol. Preferably, the glycol is an aliphatic based glycol. The preferred glycols are propylene glycol and ethylene glycol. The most preferred glycol is propylene glycol. The glycol adds humectant properties to the compositions of the present invention. A convenient source of the glycol is in the Lubrajel CG product

Amounts of the Components

The components of the present invention, are with the exception of water, determined on a solids basis unless otherwise indicated.

The weight ratio of the polyglyceryl-methacrylate to the silicone based component is typically about 75:1 to about 3:1. Preferably, the weight ratio of the polyglycerylmethacrylate to the silicone based component is about 40:1 to about 10:1, and most preferably about 35:1to 12:1.

The weight ratio of the polyglycerylmethacrylate to the polysaccharide in the liquid polysaccharide component is typically about 8:1 to about 1:2. Often, it is convenient to have weight ratio of the polyglycerylmethacrylate to the polysaccharide in the liquid polysaccharide component about 5:1 to about 1:1.

The weight ratio of the polyglycerylmethacrylate to the glycol component is typically about 10:1 to about 1:5. Preferably, the weight ratio of the polyglycerylmethacrylate to the glycol component is about 15:2 to 1:4.

The compositions of the present invention typically contain about 40 to about 90% by weight water. Preferably, the compositions of the present invention contain about 50% to about 80% by weight water.

Additional Components

In addition to the previously mentioned components, the products of the present invention may also comprise further ingredients such as, for example, perfume oils, coloring agents, and preservatives, a carrier or diluent material, and the like.

Product Usage

The products of the present invention may be formulated into lotions, shampoos, hair conditioners, sunscreens, insect repellants and the like. The level of usage in the finished compositions for consumer use is typically to apply the product at 0.1 grams to 50 grams per liter of liquid product applied or directly upon the skin or hair at 0.1 gram to 1 gram per 250 grams of hair or a similar amount to 100 square centimeters of skin surface.

EXAMPLE I

| | Weight % |
|---|---|
| Lubrajel CG | 69.40 |
| Natural Honey | 30.00 |
| Paragon III (preservative) | 0.60 |
| | 100.00 |

EXAMPLE II

| | A | B | C |
|---|---|---|---|
| | | Weight % | |
| Lubrajel CG | 69.40 | 69.40 | 69.40 |
| Honey | 26.00 | 29.00 | 28.00 |
| Dow 344 (cyclomethicone) | 4.00 | 0.00 | 0.00 |
| Dow 200 (dimethicone) | 0.00 | 1.00 | 0.00 |
| Dow 1401 (cyclomethicone and dimethiconol) | 0.00 | 0.00 | 2.00 |
| Paragon III (preservative) | 0.60 | 0.60 | 0.60 |
| | 100.00 | 100.00 | 100.00 |

The products of the above examples are substantially homogeneous viscous honey-like products with excellent skin feel and no undesirable tackiness after drying. The products may be used as a base for the creation of skin care and hair care products which feature honey ingredient chemistry with enhanced moisturizing potential. The products of the above examples exhibit the functional benefits of enhanced spreadability, slip, and substantivity.

What is claimed is:

1. A composition of matter comprising:
   polyglycerylmethacrylate; and,
   a liquid polysaccharide component selected from the group consisting of honey and corn syrup wherein the weight ratio of the polyglycerylmethacrylate to the polysaccharide in the liquid polysaccharide component is from about 8:1 to about 1:2.

2. The composition of claim 1 wherein the weight ratio of the polyglycerylmethacrylate to the polysaccharide in the liquid polysaccharide component is from about 8:1 to about 1:2.

3. The composition of claim 1 wherein the polysaccharide in the liquid polysaccharide component is a mixture of levulose and dextrose.

4. The composition of claim 1 wherein the weight ratio of the polyglycerylmethacrylate to the polysaccharide in the liquid polysaccharide component is from about 5:1 to about 1:1.

5. A composition of matter comprising:
   polyglycerylmethacrylate;
   a liquid polysaccharide component selected from the group consisting of honey and corn syrup; and,
   a silicone based component wherein the weight ratio of the polyglycerylmethacrylate to the polysaccharide in the liquid polysaccharide component is from about 8:1 to about 1:2.

6. The composition of claim 5 wherein the polysaccharide in the liquid polysaccharide component is a sugar.

7. The composition of claim 5 wherein the polysaccharide in the liquid polysaccharide component is a mixture of levulose and dextrose.

8. The composition of claim 5 wherein the weight ratio of the polyglycerylmethacrylate to the polysaccharide in the liquid polysaccharide component is from about 5:1 to about 1:1.

9. The composition of claim 5 wherein the weight ratio of the polyglycerylmethacrylate to the silicone based component is from about 75:1 to about 3:1.

10. The composition of claim 5 wherein the silicone based component is a cyclomethicone.

11. The composition of claim 5 wherein the silicone based component dimethicone.

12. The composition of claim 5 wherein the silicone based component dimethiconol.

13. The composition of claim 5 wherein the silicone based component is a cyclomethicone tetramer.

14. The composition of claim 5 wherein the silicone based component is a cyclomethicone pentamer.

15. The composition of claim 5 wherein the weight ratio of the polyglycerylmethacrylate to the silicone based component is from about 40:1 to about 10:1.

16. A composition of matter comprising:
    polyglycerylmethacrylate;
    a liquid polysaccharide component selected from the group consisting of honey and corn syrup;
    a silicone based component, and,
    a glycol wherein the weight ratio of the polyglycerylmethacrylate to the polysaccharide in the liquid polysaccharide component is from about 8:1 to about 1:2.

17. The composition of claim 16 wherein the polysaccharide in the liquid polysaccharide component is a sugar.

18. The composition of claim 16 wherein the polysaccharide in the liquid polysaccharide component is a mixture of levulose and dextrose.

19. The composition of claim 16 wherein the weight ratio of the polyglycerylmethacrylate to the polysaccharide in the liquid polysaccharide component is from about 5:1 to about 1:1.

20. The composition of claim 16 wherein the weight ratio of the polyglycerylmethacrylate to the silicone based component is from about 75:1 to about 3:1.

21. The composition of claim 16 wherein the silicone based component is a cyclomethicone.

22. The composition of claim 16 wherein the silicone based component is dimethicone.

23. The composition of claim 16 wherein the silicone based component is dimethiconol.

24. The composition of claim 16 wherein the silicone based component is a cyclomethicone tetramer.

25. The composition of claim 16 wherein the silicone based component is a cyclomethicone pentamer.

26. The composition of claim 16 wherein the weight ratio of the polyglycerylmethacrylate to the silicone based component is from about 40:1 to about 10:1.

27. The composition of claim 16 wherein the glycol is propylene glycol.

28. The composition of claim 16 wherein the polysaccharide in the liquid polysaccharide component is derived from honey.

29. A substantially homogeneous hydrated honey gel polymeric composition prepared by the process of:
    (A) dispersing honey in polyglycerylmethacrylate; and,
    (B) mixing the honey and the polyglycerylmethacrylate for a sufficient period of time to form a hydrated honey gel polymeric composition wherein the weight ratio of the polyglycerylmethacrylate to the honey from about 8:1 to about 1:2.

30. A process for preparing a substantially homogeneous hydrated honey gel polymeric composition prepared by the process of:
  (A) dispersing honey in polyglycerylmethacrylate; and,
  (B) mixing the honey and the polyglycerylmethacrylate to form a substantially homogeneous mixture, wherein the weight ratio of the polyglycerylmethacrylate to the polysaccharide in the honey is from about 8:1 to about 1:2;
  (C) combining with the substantially homogeneous mixture a silicone based component, and
  (D) mixing the resultant mixture for a sufficient period of time to form a substantially homogeneous translucent homogeneous hydrated honey gel polymeric composition.

31. The method of claim 29 wherein the silicone based component is a cyclomethicone.

32. The method of claim 29 wherein the silicone based component is dimethicone.

* * * * *